United States Patent
Zanon et al.

(10) Patent No.: US 10,648,942 B2
(45) Date of Patent: May 12, 2020

(54) ELECTROCHEMICAL CELL

(71) Applicant: Sprue Safety Products Ltd., Coventry (GB)

(72) Inventors: Mario Zanon, Coventry (GB); Ian Robins, Coventry (GB)

(73) Assignee: Sprue Safety Products Ltd., Conventry (GB)

( * ) Notice: Subject to any disclaimer, the term of this patent is extended or adjusted under 35 U.S.C. 154(b) by 411 days.

(21) Appl. No.: 15/306,228

(22) PCT Filed: Apr. 22, 2015

(86) PCT No.: PCT/GB2015/051185
§ 371 (c)(1),
(2) Date: Oct. 24, 2016

(87) PCT Pub. No.: WO2015/162418
PCT Pub. Date: Oct. 29, 2015

(65) Prior Publication Data
US 2017/0045472 A1    Feb. 16, 2017

(30) Foreign Application Priority Data
Apr. 22, 2014   (GB) .................................. 1407058.5

(51) Int. Cl.
*G01N 27/404*  (2006.01)
*G01N 33/00*   (2006.01)

(52) U.S. Cl.
CPC ....... *G01N 27/4045* (2013.01); *G01N 33/004* (2013.01)

(58) Field of Classification Search
CPC ............... G01N 27/413; G01N 27/404; G01N 27/4045; G01N 33/004; G01N 33/0044; G01N 33/0054
See application file for complete search history.

(56) References Cited

U.S. PATENT DOCUMENTS 3,719,529 A    3/1973  Lake
3,852,169 A    12/1974 Wolfe et al.
(Continued)

FOREIGN PATENT DOCUMENTS

CA    02255472 A1    6/2000
CA     2255472 A1    6/2000
(Continued)

OTHER PUBLICATIONS

United Kingdom Search Report issued by the Intellectual Property Office in connection with GB1407058.5 dated Oct. 16, 2014.
(Continued)

*Primary Examiner* — Gurpreet Kaur
(74) *Attorney, Agent, or Firm* — Levenfeld Pearlstein, LLC (57) ABSTRACT

An electrochemical cell for detecting a gas from the surrounding environment. The cell comprises an electrolyte and a sensing electrode which is in fluid communication with the electrolyte and the gas to be detected, when present. The cell further comprises a counter electrode in fluid communication with said electrolyte, and also a source of reactant gas provided in a cavity adjacent to the counter electrode, wherein reaction of the gas to be detected at the sensing electrode results in reaction of the reactant gas at the counter electrode and wherein the cavity is formed of or comprises a membrane. The cell may also have a wick extending between the sensing electrode and the counter electrode in an axial direction and a reservoir surrounding the wick.

19 Claims, 9 Drawing Sheets

(56) References Cited

U.S. PATENT DOCUMENTS

| | | | |
|---|---|---|---|
| 3,966,579 A | 6/1976 | Chang et al. | |
| 4,051,006 A | 9/1977 | Neti et al. | |
| 4,201,634 A | 5/1980 | Stetter | |
| 4,394,239 A * | 7/1983 | Kitzelmann | G01N 27/4045 204/414 |
| 5,344,546 A | 9/1994 | Kiesele et al. | |
| 5,372,696 A | 12/1994 | Kiesele et al. | |
| 6,666,963 B1 * | 12/2003 | Peng | G01N 27/404 204/412 |
| 2011/0290671 A1 | 12/2011 | Mett et al. | |
| 2013/0087457 A1 * | 4/2013 | Pratt | G01N 27/4045 204/412 |

FOREIGN PATENT DOCUMENTS

| | | |
|---|---|---|
| EP | 0172969 A2 | 3/1986 |
| EP | 1832873 A1 | 9/2007 |
| EP | 2711700 A1 | 3/2014 |
| GB | 2287791 A | 9/1995 |
| GB | 2374419 A | 10/2002 |
| GB | 2417561 A | 3/2006 |
| JP | S63071649 A | 4/1988 |
| JP | 2002048756 A | 2/2002 |
| JP | 2003513241 A | 4/2003 |
| JP | 2005083956 A | 3/2005 |
| JP | 2011141167 A | 7/2011 |
| JP | 2016564012 | 1/2019 |
| WO | 8806646 A1 | 9/1988 |
| WO | 0068676 A1 | 11/2000 |
| WO | 2004031758 A1 | 4/2004 |
| WO | 2005085824 A1 | 9/2005 |
| WO | 2010063626 A1 | 6/2010 |

OTHER PUBLICATIONS

International Search Report issued by the ISA/EPO in connection with PCT/GB2015/051185 dated Sep. 24, 2015.

European Search Report issued by ISA/EPO in connection with EP18213183 dated Feb. 11, 2019.

* cited by examiner

ELECTROCHEMICAL CELL

The present invention relates to an electrochemical cell and, in particular, but not exclusively, to an electrochemical cell for use in a gas detector.

BACKGROUND TO THE INVENTION

Amperometric electrochemical cells have found widespread use for the detection of various gases in the environment, including use for the detection of carbon monoxide in the domestic environment.

Figure 1:
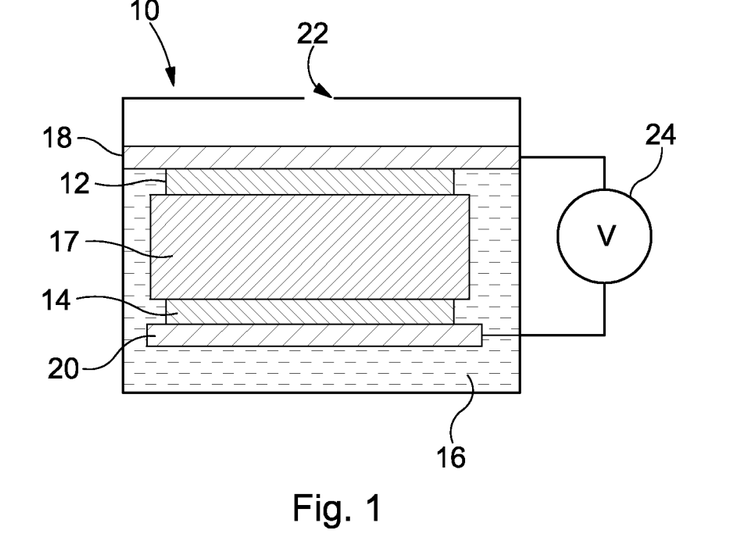
FIG. 1 is a schematic cross sectional view of an electrochemical cell.

As shown in FIG. 1, a typical cell 10 comprises two or three gas electrodes—a working or sensing electrode 12, a counter electrode 14 and, optionally, a reference electrode (not shown). In lower cost cells, the reference electrode is often omitted and the counter electrode serves as a combined counter/reference electrode. All three (two) of these electrodes comprise a very high surface area catalytic metal (or other conductive material) 12, 14 supported on a gas permeable membrane or substrate 18, 20. An electrolyte 16, for example an acid, is typically completely contained within a wick 17 at a condition of lowest humidity. The wick 17 acts to hold and supply electrolyte to the sensing electrode 12 such that the chemical reaction discussed below can occur. The cell 10 comprises a housing that defines a reservoir 11 for the electrolyte 16, in which is provided a diffusion hole 22 through which target gas can enter.

The basic principle of operation is that gas enters the cell 10 via the diffusion hole 22. The gas passes through the gas permeable membrane 18 of the sensing electrode 12 and contacts the catalyst 12. A reaction occurs at the interface of the catalyst 12 and the acid electrolyte 16 (i.e. at the intersection of gas, liquid and solid). This reaction releases or consumes a number of electrons (the precise number depending on the gas being sensed) that are supplied via an external circuit 24.

For example, in a cell configured to sense carbon monoxide (CO), the gas is oxidised at the surface of the sensing electrode 12 to produce positive hydrogen ions ($H^+$) and negative electrons ($e^-$):

The positive ions travel through the electrolyte 16 to the counter electrode 14, and the negatively charged electrons travel to the counter electrode 14 via the circuit 24. The reaction is completed at the counter electrode 14:

The overall reaction is:

The working electrode 12 is arranged such that gas from the environment enters the cell 10 and permeates through the substrate 18 where the 'target gas' present in the environmental gas (i.e. the gas that is to be sensed) reacts completely. Each gas molecule that reacts at the substrate 18 produces a fixed number of electrons (the number depending on the gas reacting) and the measurement of the current produced can then be related to the number of molecules of gas that has entered the cell and this is directly proportional to the concentration of the target gas in the environment. An ammeter, voltmeter or other circuit 24 can be used to measure/derive the current produced.

The counter and reference electrodes are, however, different. For measurement of a target gas in air, the counter/reference electrode 14 is generally configured to react with oxygen. This oxygen needs to contact the metal catalyst 14 at the interface of gas, liquid (electrolyte) and solid (catalyst). In theory, this oxygen could come from one of two places: either from air inside the cell 10 or from oxygen gas dissolved in the electrolyte 16. However, the solubility of oxygen in the electrolyte 16 is very low and the concentration of oxygen in air inside the cell 10 is relatively high and therefore oxygen from inside the cell 10 is consumed at the counter/reference electrode 14. This oxygen has to reach the metal/electrolyte interface 14, 20 by permeating through the permeable membrane 20 in order to reach the solid/liquid interface as previously described.

There are various factors that affect the efficient and reliable working and performance of an electrochemical cell.

Under certain conditions, or combinations of conditions, a degree of oxygen starvation can occur at the counter electrode 14 resulting in a decrease of the electrochemical efficiency due to the development of bias voltages. This results in a reduction of the current expected for a known concentration of the target gas, in turn resulting in an erroneous (low) reading of the gas concentration. These conditions include the orientation of the cell, the degree of hydration of the electrolyte 16 and high concentrations of the target gas for long exposure times. Furthermore, combinations of these conditions can increase the tendency for non-ideal performance, which is undesirable as it can lead to erroneous gas concentration measurements.

Acid electrolyte is generally hygroscopic in nature. That is, it will absorb or desorb water from the environment until the strength of the acid 16 is in equilibrium with the external atmospheric humidity. This absorption or desorption of water is accompanied with a change in the volume of the acid electrolyte 16. For the typical acid electrolyte used in these cells, sulphuric acid, the volume change from the typical lower operating humidity (15%) to the typical upper operating humidity (90%) can be as much as a factor of four. Therefore the design of the electrochemical cell has to be such that, at the highest operating humidity, the cell 10 is not so full that it leaks or bursts whilst, at the lowest humidity, the volume has to be large enough to ensure that the surfaces of both electrodes are fully wetted and that there is a continuous fluid path between the two electrodes (via the wick material).

Known cells all effectively comprise an axial reservoir, located either between or below the electrodes to accommodate the expansion in the electrolyte volume.

For reservoirs that are between the electrodes 12, 14, this large reservoir can produce a high internal resistance between the electrodes 12, 14 at lower humidities where the acid electrolyte is more dehydrated (and hence has a small volume) due to the relatively large distance between the electrodes and lower ionic conductivity.

For reservoirs that are below the lower electrode 14, there is sometimes the need for an additional thin piece of wick (or other wicking mechanism) to ensure that free acid is transferred into the 'main' wick 17. However, this wicking does not always occur effectively and can result in issues with repeated hydration/dehydration cycles. This is amplified by the fact that this thin piece of wick needs to be relatively long. Furthermore, positioning of this material during manufacture is complex and not easily amenable to automation.

In addition, the need for the axial reservoir imposes a certain physical structure on the cell and determines the height of the cell as approximately a minimum of 20 mm. For domestic carbon monoxide detectors, this height constricts the possible design options available for the detector.

Aspects and embodiments of the present invention have been designed with one or more of the foregoing in mind.

SUMMARY OF THE INVENTION

According to a first aspect of the present invention, there is provided an electrochemical cell for detecting a gas as defined in claim 1.

The electrochemical cell can, in principle, be used for detecting any gas, e.g. oxidisable and reducible gases. However, the electrochemical cell is most likely to be utilized in a location of standard environmental conditions, i.e. for sensing a target gas in air in the vicinity of the cell. As such, the electrochemical cell of embodiments of the present invention is particularly suited to detecting oxidisable gases, which will then require the source of reactant gas adjacent to the counter or counter/reference electrode to be a source of oxygen. The source of reactant gas adjacent to the counter or counter/reference electrode may thus be or closely resemble air. The reactant gas e.g. oxygen may be replenished by diffusion from the main cell body when the cell is idle (i.e. not detecting).

Preferably, the source of reactant gas is a gas cavity provided adjacent the counter electrode. The gas cavity may be dimensioned so as to at least partially or totally cover the counter electrode. The gas cavity is preferably dimensioned so as to provide at least a sufficient source of reactant gas to the counter electrode. Preferably, the gas cavity is sealed from the gas atmosphere outside the cell. This is because, for the reference electrode to perform well, none of the target gas must reach the reference/counter electrode. The volume of gas provided within the gas cavity may be predetermined.

The sensing electrode, counter electrode and gas cavity may be provided in a housing. Preferably, the housing is impermeable to and/or sealed from the gas atmosphere outside of the cell, apart from an inlet provided for detecting the target gas. In an embodiment, the gas cavity is provided between the counter electrode and the housing. The gas cavity may be fixed to the housing and/or sealed to the counter electrode. The gas cavity may be a flexible structure. The gas cavity may be formed by the use of a gas permeable or semi-permeable membrane that is in fluid communication with the interior of the cell. Typically, the counter electrode is mounted on a membrane or substrate. This may be the same gas permeable or semi-permeable membrane, or may be an additional membrane. In an embodiment, the gas cavity communicates gas from within the cavity with gas inside the cell. The gas cavity is preferably impermeable to the electrolyte and permeable to gases.

The electrochemical cell may further comprise a wick. The sensing electrode, wick, counter electrode and gas cavity are preferably axially aligned with respect to each other. The sensing electrode, wick, counter electrode and gas cavity may form a stack.

The counter electrode may act as a combined counter/reference electrode. The electrochemical cell may further comprise one or more additional electrodes. In an embodiment, a third or reference electrode is provided. In other embodiments, a fourth electrode that is a second sensing or working electrode may be provided.

An effect of utilizing the gas source or cavity in embodiments of the first aspect of the invention is that the "free" surface of the counter electrode, i.e. that distal from the wick, is kept free from electrolyte. This enables an increased supply of oxygen to the counter electrode than would otherwise be possible. Embodiments of aspects of the invention thus advantageously avoid oxygen starvation at the counter electrode and thus maximise the electrochemical efficiency of the cell. In such embodiments, performance is maintained irrespective of the orientation of the cell, leading to the cell being able to be used in a wider variety of installations and places.

According to a second aspect of the present invention, there is provided an electrochemical cell as defined in claim 23. The electrochemical cell can, advantageously, be used for detecting any gas, e.g. oxidisable and reducible gases.

In contrast to known prior art arrangements, where the cell comprises an axial reservoir, located either between or below the electrodes, the reservoir of the present invention surrounds the wick. In such an arrangement, the majority of the electrolyte in the reservoir is provided around the wick, peripherally, laterally, radially or circumferentially. I.e., at most, only a minority portion thereof is provided above and/or below the wick. This advantageously aids absorption of electrolyte by the wick, and thus transport of electrolyte to the electrodes.

Preferably, the reservoir extends primarily in a direction transverse to the wick. More preferably, the reservoir is an annular reservoir that surrounds the wick.

Preferably, the sensing electrode, wick and counter electrode are arranged axially with respect to each other to form a stack, and the reservoir extends primarily in a direction transverse to the stack. The reservoir preferably surrounds or at least partially surrounds the stack.

In an embodiment, a secondary wick is also provided. Preferably, the secondary wick extends transversely to the wick. The secondary wick may be or comprise a thin planar element. The secondary wick may be annular.

The sensing electrode, counter electrode and wick are preferably provided in a housing, the housing forming the reservoir. Alternatively, a separate reservoir may be provided inside the housing.

The counter electrode may act as a combined counter/reference electrode. The electrochemical cell may further comprise one or more additional electrodes. The electrochemical cell may comprise a third or reference electrode. In an embodiment, the cell further comprises one or more additional second sensing or working electrodes.

Embodiments of the second aspect of the invention avoid the need to place a reservoir between electrodes, which advantageously avoids the high internal resistance which can otherwise occur between the electrodes. The provision of a reservoir and thus the electrolyte substantially transverse to the axially arranged electrodes advantageously enables the distance between the two electrodes to be kept to a minimum which, in turn reduces the overall height of the cell, which clearly increases the utility of cells of embodiments of the invention. The arrangement of the reservoir transversely around the wick means that electrolyte can enter the wick from all sides, advantageously increasing the effective electrolyte communication path between the reservoir and the wick. This arrangement also means that the cell is completely immune from orientation effects.

According to a third aspect of the present invention, there is provided a gas detector as defined in claim 37.

In principle, the gas detector may be configured for detecting one or more oxidisable or reducible gases. In a preferred embodiment, the gas detector is configured for detecting one or more oxidisable gases. The gas detector may particularly be configured for detecting one or more of: ammonia, carbon monoxide, chlorine, diborane, fluorine, hydrazine, hydrogen, hydrogen cyanide, hydrogen fluoride, hydrogen selenide, hydrogen sulphide, hydrogen chloride, hydrogen bromide, arsine, mercaptan, nitric oxide, phosgene, phosphene, silane, or sulphur dioxide. These gases are provided by way of example only, and embodiments of the invention are not limited to the detection of these gases.

As mentioned above, in principle, embodiments of the invention can also be utilised to detect a reducible gas. In such embodiments, the reactant gas may be or contain hydrogen. In such embodiments it may be difficult to replenish the reactant gas from gas inside the cell and it may then necessary to provide an additional reactant gas replenishing source.

The embodiments and aspects of the invention described above may be utilised in any combination within the same electrochemical cell and/or gas detector. For example, an electrochemical cell may comprise the features of both claims 1 and 23, and optionally any or all of the claims dependent thereon. Such a cell may be utilised in a gas detector according to embodiments of the third aspect of the invention.

BRIEF DESCRIPTION OF THE FIGURES

Embodiments of the invention will now be described with reference to the following drawings, in which.

DETAILED DESCRIPTION OF EMBODIMENTS OF THE INVENTION

Figure 2:
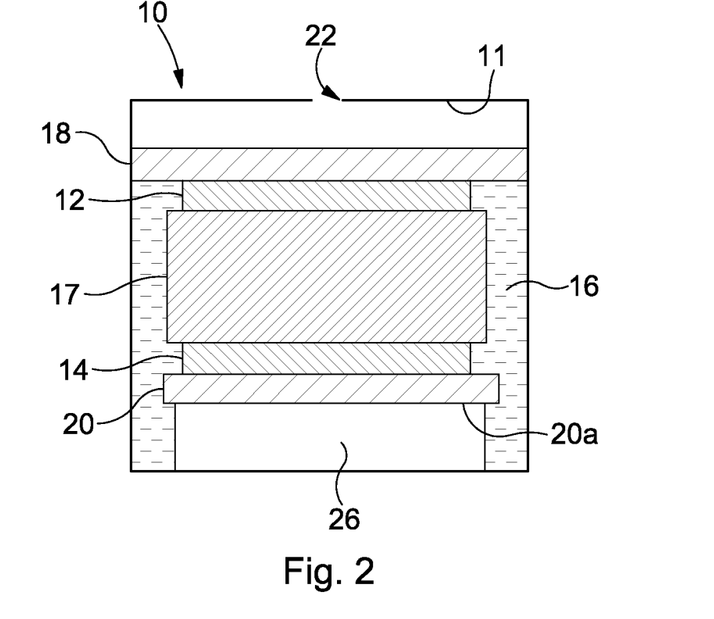
FIG. 2 is a schematic cross sectional view of an electrochemical cell according to an embodiment of the invention.
Figure 3:
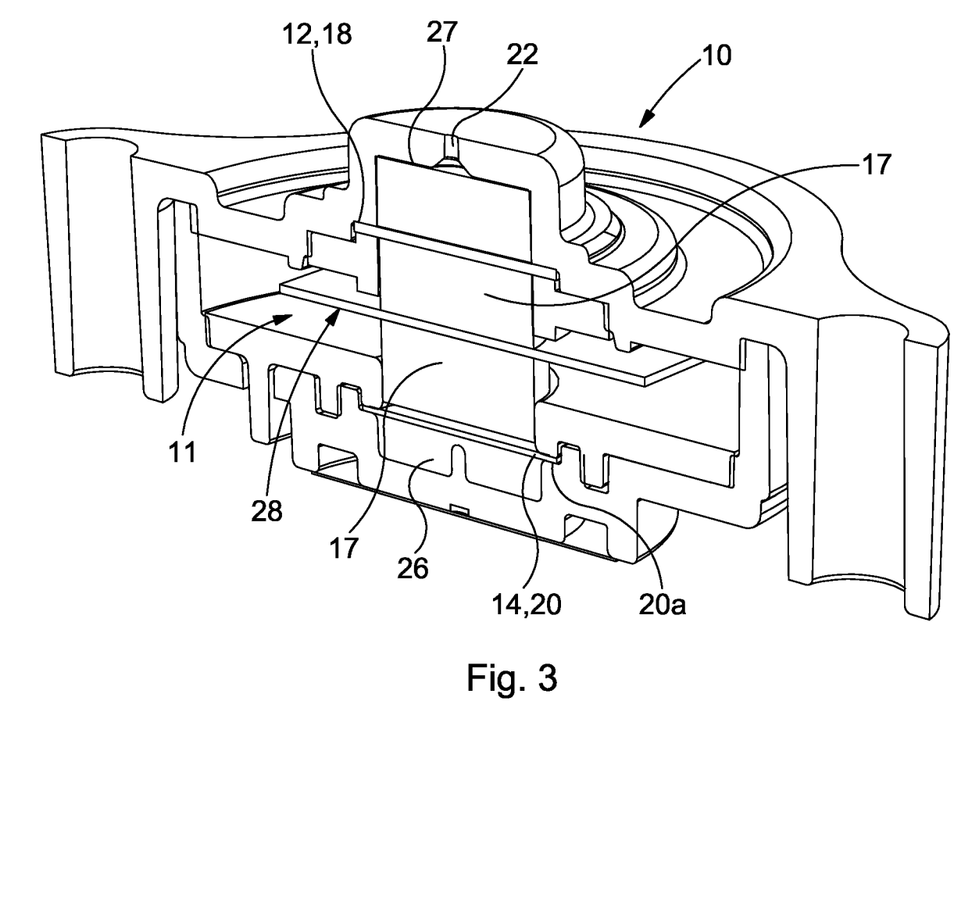
FIG. 3 is a perspective cross sectional view of an electrochemical cell according to an embodiment of the invention.
Figure 4:
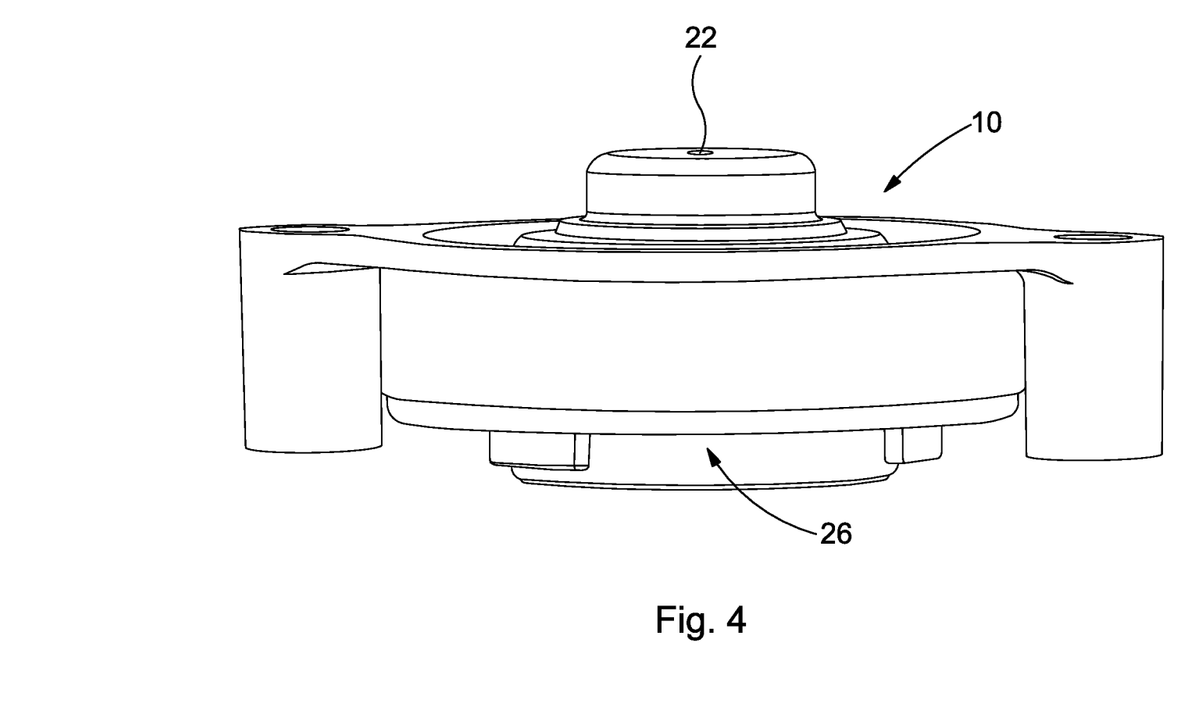
FIG. 4 is a front perspective view of an electrochemical cell according to an embodiment of the invention.

A first aspect of the invention can be embodied in a number of different ways, but FIGS. 2 to 4 show an exemplary basic structure of an embodiment of the present invention. Features in common with the conventional arrangement described above are depicted using like reference numerals. It can be seen that an electrochemical cell 10 comprises a sensing electrode 12, and a counter or counter/reference electrode 14. Although not shown, a separate reference electrode may be provided whereby the electrode 14 then acts purely as a counter electrode.

Each electrode 12, 14 preferably comprises a very high surface area catalyst 12, 14 supported on a respective gas permeable membrane 18, 20. The membrane 18, 20 may be porous PTFE. The catalyst 12, 14 may be a metal, such as a finely divided platinum catalyst, or other conductive material e.g. graphite. A small amount of PTFE bonding material may be utilized to bond the catalyst 12, 14 to the membrane 18, 20.

The electrodes 12, 14 are in contact with a liquid electrolyte 16. The electrolyte 16 may be an acid, e.g. sulphuric acid. In other embodiments, the electrolyte may be alkaline or neutral. A water electrolyte may be used and even non-aqueous electrolytes can be used in certain cells. The electrolyte 16 is typically largely contained within a wick 17 at a condition of lowest humidity. The purpose of the wick 17 is to ensure fluid communication between the electrolyte 16 and the electrodes 12, 14. The wick 17 may be formed of a glass fibre material. Typically, therefore, the cell components are "stacked". On the counter electrode substrate 20 is provided the conductive layer 14, with the wick 17 adjacent thereto. The conductive sensing electrode 12 is provided adjacent the wick 17, and on the opposite surface of which is the sensing electrode substrate 18. The orientation shown in FIGS. 2 to 4, with the components arranged vertically and with the counter electrode 14 lowermost, is not limitative, and embodiments of the invention can be used in other orientations.

The embodiments described above and shown in FIGS. 2 and 3 comprise two electrodes 12, 14, although a third, reference electrode (not shown) could also be included. The counter electrode 14 need not then be used as a combined counter/reference electrode. In other embodiments, also not shown in the Figures, the cell 10 may include more electrodes. For example, the cell 10 could comprise four electrodes: two working/sensing electrodes, a counter electrode and a reference electrode. Such cells can be used for the detection of two gases simultaneously.

The cell 10 comprises a housing in which is provided a diffusion hole 22 through which target gas can enter. The housing 10 may be formed of a plastics material, e.g. ABS (acrylonitrile butadiene styrene), carbon-filled ABS, or any other material that is resistant and impermeable to the electrolyte 16. The housing forms a reservoir 11 for the electrolyte 16. Alternatively, a separate reservoir enclosure may be provided within the housing 10. In either case, one or more additional sealing and/or filter means 27 (as shown in FIG. 3) may be provided in or in the vicinity of the diffusion hole 22. The filter 27 can filter out any unwanted gases that are not desired to reach the electrode 12 or to permit a gas to be sensed to enter the chamber 11. The filter 27 or a sealing member can further assist in containing the electrolyte 16 within the housing/reservoir 11. The sensing electrode 12 can also be sealed to the cell body such that electrolyte 16 cannot encroach above the electrode 12.

The cell 10 and the components thereof may take a variety of forms. In one embodiment, the PTFE membranes of the electrode substrates 18, 20 may have a thickness of about 140-250 microns. Each electrode 12, 14 may be approximately 3 mm to 25 mm in diameter. In one embodiment, the diameter is approximately 5 mm. The height of the catalyst layer 12, 14 may typically be between about 10 to 100 μm. The thickness of the wick 17 may be between about 0.25 mm to 20 mm. In one embodiment, the thickness is approximately 5 mm.

The electrodes 12, 14, substrates 18, 20, reservoir 11/housing 10 and wick 17 are preferably round/cylindrical (as shown in FIGS. 3 and 4) but, in alternative embodiments, may be differently configured.

In the embodiments of FIGS. 2-5 a gas source, e.g. a cavity 26 is also provided. In the embodiment shown the gas cavity 26 is in fluid communication with the gas inside the cell 10. Embodiments of the invention may most usefully be employed in standard atmospheric conditions, i.e. where the cell 10 is surrounded by air. As such, the gas inside the gas cavity 26 will typically be air or comprise constituents similar to air. When used in such standard conditions, the sensing electrode 12 of the cell 10 will be configured to react with an oxidisable gas, and the counter electrode 14 will be configured to react with oxygen. Reference from hereon will thus primarily be directed to embodiments where the cell 10 is utilised in standard conditions, but it should be appreciated that protection is not limited thereto.

The gas source/cavity 26 is in fluid communication with the counter electrode 14 and preferably positioned adjacent, e.g. behind or below the counter electrode 14. Electrolyte 16 cannot enter the air cavity 26, although the gas permeable membrane 20 permits oxygen (and other gases) to enter the cavity 26. An additional gas permeable/semi-permeable membrane or layer (not shown) may also be provided to seal the cavity 26, e.g. to allow the electrode 14, 20 and cavity 26 to be constructed separately. The cavity 26 therefore prevents the electrolyte 16 in the cell 10 from covering the rear of the counter electrode 14. This prevents oxygen starvation at the counter electrode 14, which could otherwise occur if the electrolyte were to completely cover the rear of the electrode 14 and therefore prevent gas access. The sealed nature of the cavity 14 means that the cell 10 is immune to orientation and hydration issues, as will be discussed in greater detail below.

The gas cavity 26 does not need to cover the whole of the rear 20a of the counter electrode 14, but does need to provide enough "open area" to ensure that oxygen starvation cannot occur. It is preferable to ensure as large an area is provided as possible. In the embodiment of FIG. 2 or 3, the gas cavity 26 covers the majority of the rear 20a of the counter electrode 14, but could alternatively cover the entire rear 20a of the counter electrode 14. The volume of the cavity 26 can be chosen so as to provide the amount of oxygen required to ensure the cell 10 continues to operate within expected performance characteristics under extreme conditions. The area of the counter electrode surface 20a that the cavity 26 needs to cover depends on the amount of target gas the cell 10 is likely to be required to detect. By way of an example, for a CO cell 10 in a domestic environment, the typical alarm time at 400 ppm (parts per million) is 3 minutes. A cavity 26 having a depth of about 1 mm, but covering the majority of the electrode area, ensures that at 400 ppm for 4 hours, less than 10% of the available oxygen in the cavity 26 is consumed. The cavity 26 volume/dimensions may also be chosen depending on the desired size and configuration of the cell 10. For example, if the overall height of the cell 10 is desired to be kept to a minimum, a wider, shorter cavity 26 may be provided.

Figure 5:
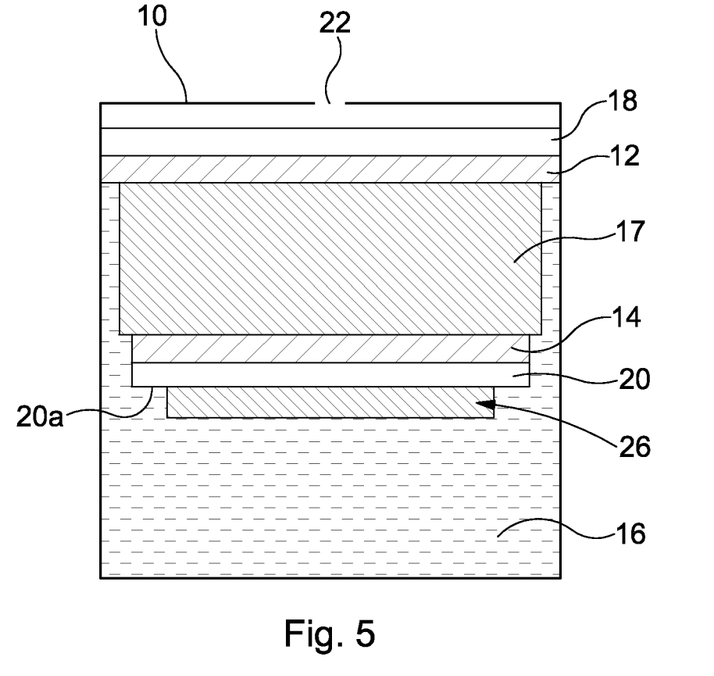
FIG. 5 is a schematic cross sectional view of an electrochemical cell according to another embodiment of the invention.

In the embodiment of FIG. 2 or 3, the cavity 26 is a sealed area between the rear 20a of the counter electrode 14 and the base of the cell housing 10. The cavity 26 may be or comprise a hollow, e.g. tubular member or may be a container that is open across one surface thereof. The electrode 14, 20 is secured to the cavity 26. If needed, the cavity 26 can be secured to the interior of the housing. Securing of the cavity 26 may be achieved by a number of different means, e.g. by clamping, sealing, welding, gluing or fixing with a gasket. The cavity 26 does not need to be fixed to the base of the cell body 10, but could be sealed to the rear 20a of the counter electrode 14 as a free standing structure within the cell body 10, as shown in FIG. 5. Alternatively, although not shown in the Figures, the gas cavity 26 could be formed completely from a gas permeable membrane and therefore be a completely flexible structure. In an embodiment, the cavity 26 can be formed by an elongate strip of flexible gas permeable material, curved round such that the two free ends thereof meet or are joined together (using any suitable means) to form an annular/tubular structure defining the cavity 26 therein. The circumferential surface area can provide a good fluid communication path for replenishing the cavity 26 with oxygen from elsewhere inside the cell 10 after it has been reacted at the counter electrode 14, as discussed further below.

In order for the counter electrode 14 to operate effectively, oxygen gas needs to enter the counter electrode 14 by passing through the permeable membrane 20. For this to occur, at least a portion of the rear surface 20a of the counter electrode 14 needs to be "dry", i.e. free from electrolyte. Otherwise, the electrolyte 16 would prevent oxygen gas passing into the membrane 14 and to the counter electrode 14.

Dryness of at least part of the rear surface 20a of the counter electrode 14 is achieved through the provision of the adjacent gas source or cavity 26 providing a necessary source of oxygen. As oxygen in the cavity 26 is consumed when the cell 10 is detecting gas, as described above, the gas cavity 26 must be replenished with oxygen in order for the cell 10 to continue to operate effectively. The cavity 26 is sealed from the environment outside of the cell 10, and so the oxygen can only be replenished from inside the cell 10. Since it is undesirable for electrolyte 16 to enter the cavity 26, the cavity 26 may be or comprise a semi-permeable membrane, as previously mentioned. In most practical embodiments, the gas outside of the cell 10 is air. The cavity/membrane 26 is in fluid contact with the gas that is inside the cell 10, and the cell 10 is in fluid contact with air external to the cell 10 via the diffusion hole 22. As such, the gas inside the cavity 26 will also be air (or a gas that is related to/resembles air, since the semi-permeable membrane may cause a slight difference in the actual composition of gases within the cell).

A potential problem can arise if there is any free electrolyte 16 in the cell 10 (i.e. not contained within the wick) because, depending on the orientation of the cell, this free acid 16 could cover the rear 20a of the counter electrode 14 if there was no sealed cavity 26 in place. In the arrangement of FIG. 2 or 3, this could occur when the cell 10 is oriented with the diffusion hole 22 upwards. Other configurations are known, but these also suffer from the same effects. For example, cells are known in which the working and counter electrodes are provided on a single planar substrate. Cells of this kind suffer the same fate if the cell is oriented with the diffusion hole downwards. In addition, if the electrode 14, 20 is placed directly against a solid surface, e.g. the cell housing 10, this could also prevent gas entering the rear of the electrode 20, so it is beneficial for the electrode 14, 20 to be spaced from the cell housing 10.

Therefore, for electrochemical cells, orientation can have a dramatic effect on cell performance under certain circumstances. However, as the orientation of any detector (containing a cell) cannot be guaranteed, then this represents a performance risk for these cells.

Figure 6:
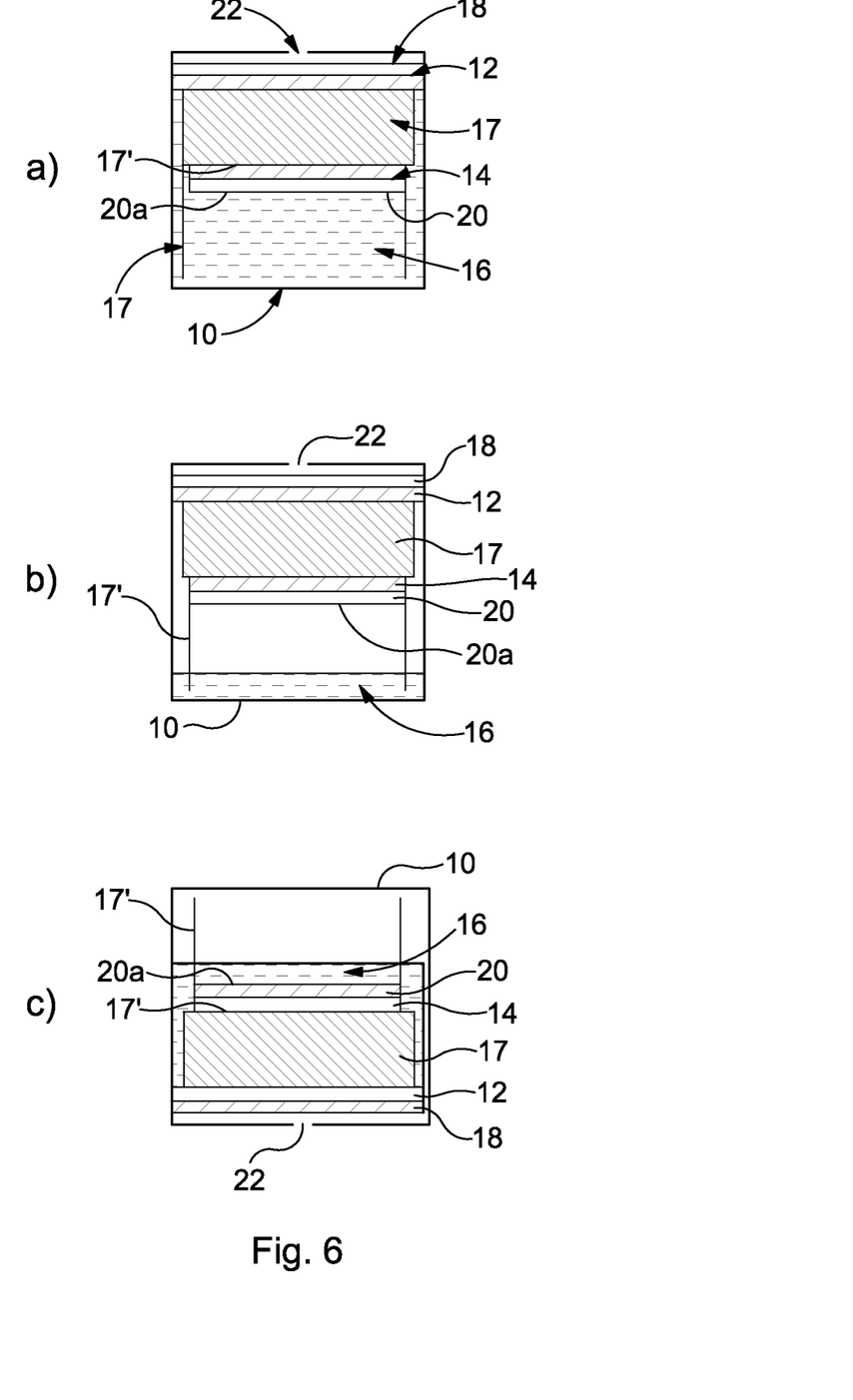
FIGS. 6(a) to (c) are schematic cross sectional views illustrating a known electrochemical cell in various hydration and orientation conditions.

This is illustrated in FIG. 6, which demonstrates the issues that arise for a known cell that does not include a cavity 26 adjacent the counter electrode 14. FIG. 6(a) shows the "fully hydrated" situation, where electrolyte 16 fully covers the rear of the counter electrode 14. Although there will be a small amount of air/oxygen dissolved in the electrolyte, this is unlikely to be a sufficient oxygen source for the counter electrode under a "high use" where a large amount of target gas is being sensed. The electrolyte 16, therefore, prevents air that would otherwise be able to reach the counter electrode 14 from doing so. The known cell comprises an additional wick 17' that still provides a path for electrolyte 16 to the sensing electrode 12 even in a minimum hydration condition such as that shown in FIG. 6(b). The additional wick 17' comprises a portion that sits between the main wick 17 and the counter electrode 14. Embodiments of the present invention could also be provided with an additional wick.

FIG. 6(b) illustrates the situation where there is minimum hydration in the cell 10. Here, the rear 20a of the electrode 14 is dry and a maximum volume of air/oxygen is available to feed to the counter electrode 15 as air/oxygen is readily available within the cell and at the counter electrode 14.

FIG. 6(c) illustrates the scenario where the cell 10 is inverted, as may well be required in some sensing locations. Even though there is a low volume of electrolyte 16 (as in FIG. 6(b), it still covers the rear 20a of the counter electrode 14 and thus prevents oxygen access through the semi-permeable membrane 20.

Another factor that can affect the performance of a cell is the degree of electrolyte hydration. The electrolyte 16 in the cell 10 is in dynamic equilibrium with the environment and will typically be hygroscopic. This means that the electrolyte 16 will absorb or lose water (slowly) depending on the external atmospheric humidity via the diffusion hole 22 in the cell 10. Under high humidity conditions, the electrolyte 16 will absorb water and, as a result, the volume of the electrolyte 16 will increase. For example, for a cell 10 designed to operate between 15% and 90% rH (relative humidity), this can equate to a change in electrolyte volume of over 400% between these extreme conditions. Therefore, when the cell 10 is placed in a high humidity environment for a long period of time, the chance of the electrolyte 16 covering the rear 20a of the counter electrode 14, and therefore preventing oxygen reaching the electrode 14, increases dramatically.

The provision of an air cavity 26 adjacent the rear 20a of the counter electrode 14 prevents the electrolyte 16 from covering the rear 20a of the counter electrode 14, and thus prevents a drop in performance that may otherwise occur.

A further factor that can affect cell performance is long exposure of the cell 10 to high concentrations of the target gas.

Under normal working conditions for any gas sensor, the quantity of oxygen reaching the counter electrode 14 is sufficient to ensure that the cell 10 is producing a current that is directly related to the concentration of gas reaching the working electrode 12. However under more exceptional conditions—e.g. a high concentration of the target gas for an extended period of time—the amount of oxygen required at the counter electrode 14 exceeds the amount of oxygen that can reach the counter electrode 14 through the counter membrane 20. When this occurs, the current output from the cell 10 decreases. Once the cell 10 is returned to a clean environment (i.e. with no target gas present), then the cell 10 recovers. This can, however, take a finite time depending on how long it takes for the oxygen environment around the counter electrode 14 to return to its ambient conditions.

The provision of an air cavity 26 on the rear 20a of the counter electrode 14, however, provides a larger source of oxygen for the counter electrode 14 such that a situation of oxygen starvation is only reached under very extreme conditions. The cell 10 is thus able to operate with good, consistent performance over a wider range of conditions than a cell that does not have an air cavity.

The effect of these different issues can be compounded when one of more of these conditions occur simultaneously. For example, in high humidity conditions and "bad" orientation, the counter electrode 14 can be completely covered with electrolyte 16 and thence oxygen starvation can occur even under normal operating conditions.

Referring again to FIG. 5, under the conditions illustrated, the electrolyte 16 is in equilibrium with gas outside the cell, excluding any oxidisable gases that will be consumed at the sensing electrode. Hence, as mentioned previously, air will be dissolved (in small amounts) in electrolyte 16. The cavity 26 is an impermeable structure fixed to the rear 20a of the counter electrode 14. Since the electrode membrane 20 is semi-permeable, liquid cannot permeate therethrough into the cavity 26, but gas such as gases including oxygen can. Gas, e.g. oxygen, enters the cavity 26 having permeated through the semi-permeable membrane 20, and is therefore in equilibrium with gas/oxygen in the liquid electrolyte 16. Since the electrolyte 16 has air/oxygen dissolved in it, this air/oxygen will pass into the cavity 26 until an equilibrium position is achieved.

So, during operation of the cell 10, air and a target gas (if present) enters the cell 10 through the diffusion hole 22. The sensing electrode 12 reacts with any oxidisable gases and converts them to a fully oxidised form (e.g. CO→CO2). Air with any oxidised gases will dissolve in small amounts in the electrolyte 16 and also enter any areas inside the cell 10 that is not full of electrolyte 16. Any gases dissolved in the electrolyte 16 will slowly permeate through the semi-permeable membrane 20 and the gas composition in the cavity 26 will equalise with the external gas composition, minus any oxidisable gases.

Irrespective of the hydration or orientation conditions, the air cavity 26 will always provide a ready source of oxygen for the reaction that occurs at the counter electrode 14. Under conditions of high use (e.g. 400 ppm for 4 hours), the gas cavity 26 provides a large source of oxygen—far higher than could be provided from the electrolyte 16 alone.

Figure 7:
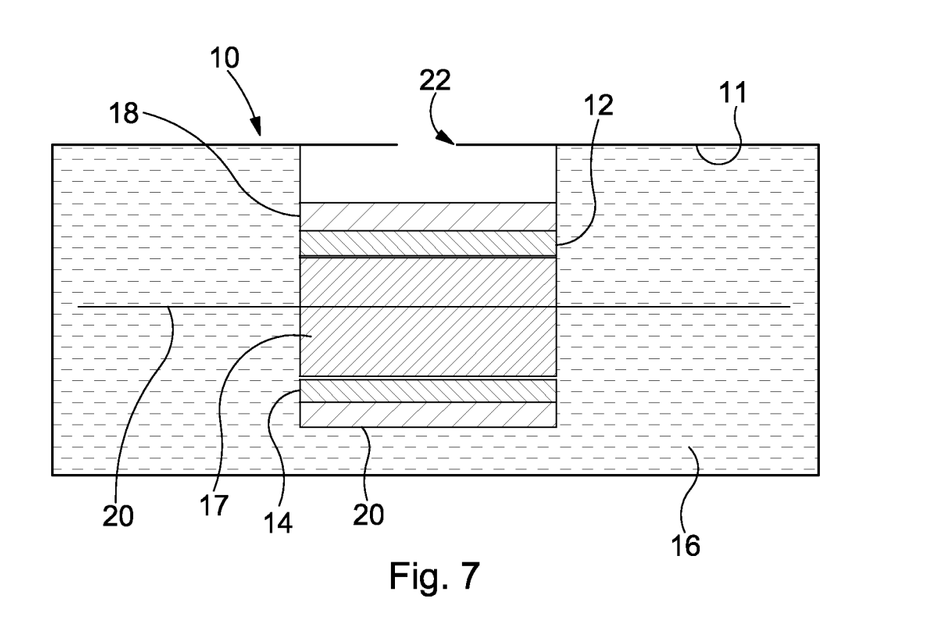
FIG. 7 is a schematic cross sectional view of an electrochemical cell according to another embodiment of the invention.

According to a second aspect of the present invention, for example as shown in FIGS. 3, 4 and 7, the reservoir 11 of electrolyte 16 extends primarily around the main wick 17 rather than above or below it. In some embodiments, the reservoir 11 does not extend above or below the (upper and lower) ends of the main wick 17; in others it may do but the majority of the electrolyte 16 is located transversely around the axial wick 17. In some embodiments, the reservoir 11 extends primarily around the stack formed by the electrodes 12, 14 and main wick 17, rather than above or below the stack 12, 14, 17. That is to say, the majority of the electrolyte 16 and reservoir 11 is provided peripherally, laterally, radially or circumferentially around the wick 17 or the stack, with only a minority portion thereof, at most, being provided above and/or below the wick 17 or stack 12, 14, 17.

The majority of the electrolyte 16 is thus provided around the wick 17 or the stack 12, 14, 17, encircling it. This is in contrast to known prior art arrangements, in which the electrolyte/reservoir is provided between or below the electrodes. NB. The electrolyte 16 cannot surround the working/sensing electrode 12 completely since gas could not then access the electrode 12 and the cell 10 would not be workable. The electrolyte 16 may, however, partially surround or extend peripherally around the sensing electrode 12. The embodiment of FIG. 7 is shown with the reservoir 11 surrounding the entire stack, but with the area above the sensing electrode 12 devoid of electrolyte 16. Alternatively, this area could be increased or decreased, or the electrolyte 16 could surround less of the stack, e.g. as in the embodiment of FIG. 3, depending upon requirements. It is, however, permissible for the electrolyte 16 to effectively completely surround the counter electrode 14, e.g. as shown in FIG. 1 (i.e. to the maximum extent possible given the adjacent components). Alternatively, the electrolyte 16 may only partially surround the counter electrode 14.

The cell 10 further comprises an additional or secondary wick 28, to ensure electrolyte 16 in the reservoir 11 is available to the main wick 17 and thus to the electrodes 12, 14. Like the reservoir 11, the additional wick 28 extends transversely to the direction of the stack 12, 14, 17. In an embodiment, the additional wick is annular and sits around the main wick 17. In alternative embodiments, the additional wick 28 could be differently shaped, e.g. be square, rectangular, or oval etc. in shape, and have a regular or irregular form.

The simple re-arrangement of the position of the reservoir 11 from below the electrode 14 (or between the electrodes 12, 14) to around the wick 17 or the electrode stack 12, 14, 17 has the following advantages.

The use of a circumferential reservoir 11 advantageously enables the main wick 17 to remain short. This arrangement allows the distance between the two electrodes 12, 14 to be kept relatively small, which overcomes the issue of high internal resistance described above, whilst achieving an effective electrolyte communication path between the reservoir and the wick 17.

Furthermore, as the volume of an annulus increases with the square of the radius, this arrangement permits a relatively large reservoir to be created for only a relatively small increase in radius.

In known electrochemical cells having a reservoir below the lower electrode, it is known to utilise an additional thin piece of wick comprising a planar portion and two portions extending perpendicularly therefrom downwardly into the reservoir. A disadvantage of such arrangements is that the overall height of the cell is, inevitably, quite high, which will not be suitable for use in some situations. By contrast, embodiments of the present invention utilise a short length of thin wick material 28, ensuring that similar issues known to be associate with the long thin wick of other structures is eliminated. The radial reservoir 11 thus enables cells to be made that are substantially shorter than any cells that are currently available. This permits a wider range of design options for the detector into which the cell is to be fitted.

Importantly, the arrangement of the reservoir 11 surrounding the wick 17 (e.g. in an annular reservoir 11) means that electrolyte 16 can enter the wick 17 from all sides therefore making exchange of electrolyte 16 to the wick 17 from the reservoir 11 more effective.

In addition, the reservoir 11, being an annulus around the wick 17, means that the cell 10 is completely immune from orientation effects, as opposed to the other known designs where certain orientations mean that communication of electrolyte from the reservoir into the wick is more difficult.

The issue of water uptake or loss to equilibrate with the ambient humidity occurs for all hygroscopic electrolyte cells and, as such, cells according to embodiments of the present invention will be subjected to effects of this kind irrespective of where and how they are used. In some ways, the constraints of the domestic environment means that cells according to embodiments of the present invention may be in a more controlled environment than those used in other applications. There is, therefore, scope for embodiments of the invention to have greater application outside of the domestic environment. These more severe conditions include areas including, for example, industrial applications where detectors will other be taken into environments that have 100% rH (relative humidity).

The cell 10 of aspects and embodiments of the present invention may be operated in amperometric mode using a high impedance op-amp circuit, as is known in the art, and as will be discussed in relation to FIG. 8 below. The electrochemical cells 10 of embodiments of the invention described above can be utilised, inter alia, in gas detectors. A wide range of target gases can be detected including, oxidisable gases such as, but not limited to, ammonia, carbon monoxide (CO), diborane, fluorine, hydrazine, hydrogen ($H_2$), hydrogen cyanide, hydrogen fluoride, hydrogen selenide, hydrogen sulphide ($H_2S$), hydrogen chloride (HCl), hydrogen bromide (HBr), arsine ($AsH_3$), mercaptan, nitric oxide, phosgene, phosphene ($PH_3$), silane, sulphur dioxide ($SO_2$), or chlorine ($Cl_2$). As mentioned above, it is also possible that embodiments of the invention could be utilised for detecting reducible gases such as chlorine dioxide, ethylene oxide, nitrogen dioxide, oxygen, and ozone.

Of particular interest in both the domestic and commercial market are carbon monoxide (CO) detectors. CO detectors are designed to measure CO levels over time and raise an alarm before a predetermined level is reached. Detectors of this kind are particularly useful since CO is either difficult or impossible to detect without specialised detection equipment and is potentially dangerous, sometimes fatal, to humans. From a practical point of view as discussed above, embodiments of the invention can be incorporated into any cell that works on the principle of oxygen consumption at the counter electrode.

An electrochemical cell 10 according to aspects of the present invention can be utilised in a gas detector, e.g. a CO detector. During operation, the current produced by the cell 10 is related to the concentration of CO (or other gas) in the atmosphere. Advantageously, electrochemical cells 10 of embodiments of the present invention can be incorporated into gas (e.g. CO) detectors in place of existing electrochemical cells in a conventional way without any modifications.

The cell 10 can be configured to be matched to the target concentration of gas to be detected. The cell 10 may comprise a chemical filter 27 (visible in FIG. 3), for filtering out unwanted gases. This enables a specifically located cell 10 to reliably detect the target gas. Embodiments of aspects of the present invention are capable of, and designed to be exposed to, any concentration of gases, including those that are higher than normally experienced. The cell may be configured to detect less than 10,000 ppm of the target gas, and preferably lower than 1,000 ppm, which is the level at which CO becomes poisonous to humans for short exposure times, but is not limited to this.

For aspects/embodiments of the invention comprising a reservoir 11 surrounding the wick 17 or the electrode stack, this has been found advantageously to provide cells that work at least to the same performance level as known cells that are twice the height. There may be locations in which a cell is desired to be placed that cannot easily accommodate a taller cell, or where the cell may be more likely to be damaged due to the larger protrusion. Thus, the change in geometry from an axial to a surrounding reservoir has clear advantages.

Figure 8:
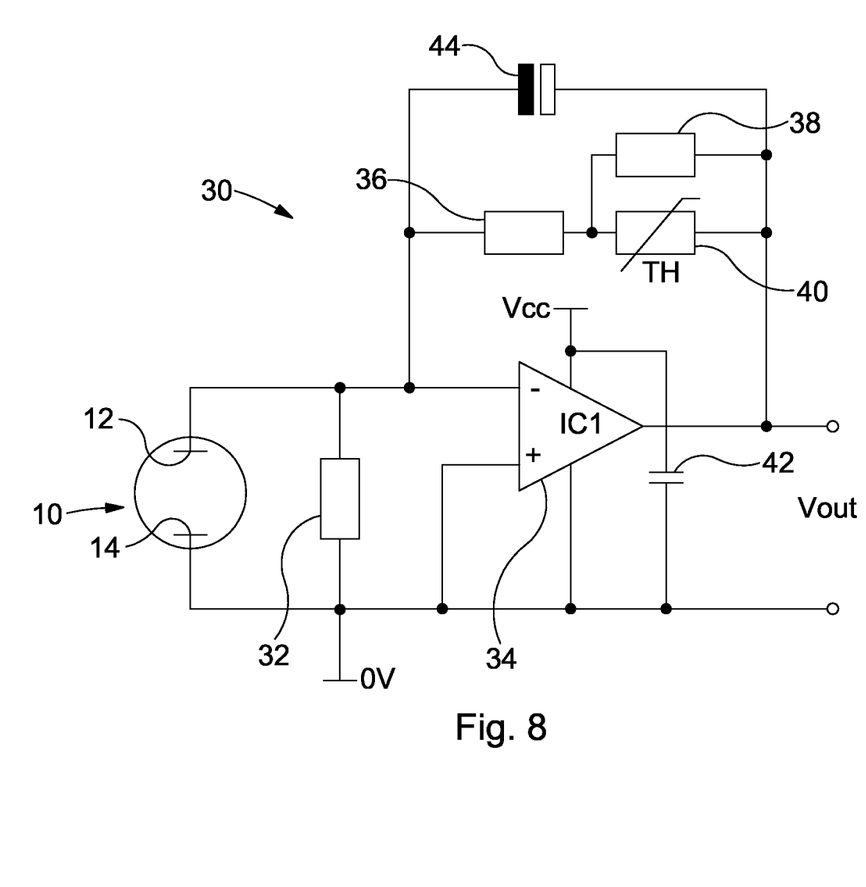
FIG. 8 is an exemplary control circuit for a carbon monoxide detector incorporating an electrochemical cell according to an embodiment of the invention.

FIG. 8 shows an exemplary control circuit 30 that may be employed in a CO detector incorporating the two- (or three-) electrode cell 10. The circuit 30 is a simple potentiostat circuit for driving the cell 10, as would be understood by those skilled in the art. The cell 10 is shown on the left hand side of FIG. 8, from which it can be seen that the working (sensing) and counter electrodes 12, 14 are connected to the circuit 30.

In operation, the electrochemical cell 10 will produce a current when exposed to the target gas, and this current is directly related to the concentration of gas the cell is exposed to. This current flows through a resistor 32, generating a small voltage difference across the cell 10. An operational amplifier (op-amp) 34 is provided to regulate the electrode 12, 14 potentials and ensure the sensor 30 can operate at maximum efficiency. Any op-amp having low input offset voltages meaning the cell electrodes are not biased can be utilized. The op-amp 34 provides a feedback voltage to the working electrode to balance the small voltage generated across the cell 10. The voltage generated, $V_{out}$, is therefore directly related to the current flowing through the cell 10 and therefore directly related to the concentration of target gas the cell 10 is exposed to.

Two resistors 36, 38 control the gain of the op-amp 34. A thermistor 40 can optionally be provided to compensate for temperature effects in the cell 10 and circuit 30. Capacitors 42, 44 are provided for reducing noise in the circuit 30.

Figure 9:
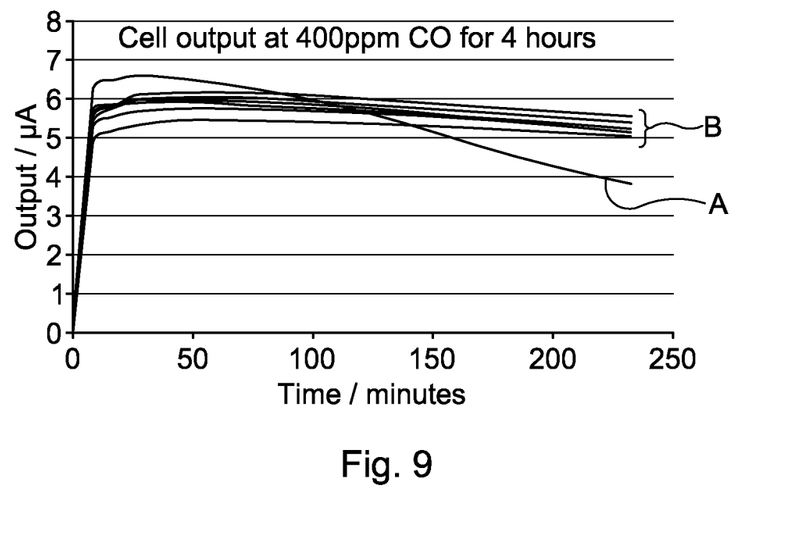
FIG. 9 illustrates performance results obtained using cells of embodiments of the invention compared with a reference.

FIG. 9 illustrates the effect that the provision of a gas cavity 26 has on performance of the cell 10. The graph shows results of placing cells in a test chamber and exposing them to 400 ppm CO (400 parts per million of Carbon Monoxide) for four hours. The graph shows the current output in microamps on the vertical axis and the elapsed time in minutes on the horizontal axis. For an ideal sensor, the current generated is directly proportional to the gas concentration. The current output for an ideal detector would thus be a horizontal line on the graph of FIG. 9.

Plot A is a control result showing the output from a cell with no gas cavity 26. The five plots labelled B are results from cells according to the present invention with gas cavities 26 of different sizes, ranging from 1 mm to 4 mm. The gas in the cavity 26 initially was air although, as explained above, the composition of the gas within the cavity 26 can change slightly over time. It should be noted that the cells providing the results for the 'B' plots were designed to provide an alarm at 400 ppm CO within 3 minutes.

The graph of FIG. 9 clearly shows that the current output of the cell that provided the result for plot A decreases significantly over time, whereas the results for the cells having an air cavity show a current output that is much more stable and which does not decrease significantly over time. Clearly, since a constant gas concentration is being applied in this test, there is a slight deviation of the 'B' plots away from the horizontal, but the results clearly show an improvement on known cell structures. I.e., by having a sealed cavity 26, the cell 10 does not suffer from the effects of electrolyte volume (due to high humidity) or flooding (due to orientation effects). The 'B' plots also show that, within the confines of this test, there is little difference between the four results. That is to say, the size of the cell used did not have a significant effect on the performance of the cell. Generally speaking, the provision of a gas cavity e.g. an air gap of any size vastly improved the performance of the cell over cells having no gas cavity or air gap.

For the avoidance of doubt, the various aspects and embodiments, and features and components relating thereto, herein described can be utilised in any combination. For example, an electrochemical cell can comprise any or all of the features of the first aspect defined in claims 1 to 22 below together with any or all of the features of the second aspect defined in claims 23 to 36 below. A gas detector can comprise an electrochemical cell having such a combination of features.

The invention claimed is:

1. An electrochemical cell for detecting a gas from a surrounding environment, the cell comprising:
    an electrolyte;
    a sensing electrode in fluid communication with said electrolyte and said gas to be detected, when present;
    a counter electrode in fluid communication with said electrolyte;
    a source of reactant gas provided in a cavity adjacent to the counter electrode, wherein reaction of said gas to be detected at the sensing electrode results in reaction of the reactant gas at the counter electrode,
    wherein the cavity is formed of or comprises a gas permeable or gas semi-permeable membrane configured for replenishment of the reactant gas with gas from the electrolyte through the gas permeable or gas semi-permeable membrane, and
    wherein the cavity is sealed from the gas from the surrounding environment.

2. The electrochemical cell of claim 1, wherein the cavity is one of a flexible structure or a rigid structure.

3. The electrochemical cell of claim 1, wherein the cavity is dimensioned so as to at least partially or totally cover the counter electrode.

4. The electrochemical cell of claim 1, wherein the source of reactant gas is impermeable to the electrolyte and/or permeable to gases.

5. The electrochemical cell of claim 1, wherein the reactant gas in the source of reactant gas is or comprises oxygen.

6. The electrochemical cell of claim 1, further comprising a wick, wherein the sensing electrode, wick, counter electrode and source of reactant gas are axially aligned with respect to each other to form a stack.

7. The electrochemical cell of claim 1, further comprising a third or reference electrode.

8. The electrochemical cell of claim 1, further comprising one or more additional sensing or working electrodes.

9. The electrochemical cell of claim 1, wherein the counter electrode is a combined counter and reference electrode.

10. An electrochemical cell for detecting a gas, comprising:
    a reservoir containing an electrolyte;
    a sensing electrode in fluid communication with said electrolyte and said gas to be detected, when present;
    a counter electrode in fluid communication with said electrolyte;
    a cavity adjacent to the counter electrode, wherein the cavity is formed of or comprises a gas permeable or gas semi-permeable membrane configured for replenishment of a reactant gas with gas from the electrolyte through the gas permeable or gas semi-permeable membrane; and
    a wick extending between the sensing electrode and the counter electrode in an axial direction to provide a communication path for the electrolyte therebetween, wherein the reservoir surrounds the wick.

11. The electrochemical cell of claim 10, wherein the reservoir is an annular reservoir that surrounds the wick.

12. The electrochemical cell of claim 10, wherein the sensing electrode, wick and counter electrode are arranged axially with respect to each other to form a stack and the reservoir extends primarily in a direction transverse to the stack.

13. The electrochemical cell of claim 10, further comprising a secondary wick extending transversely to the wick.

14. The electrochemical cell of claim 13, wherein the secondary wick is or comprises a thin planar element.

15. The electrochemical cell of claim 13, wherein the secondary wick is an annular wick.

16. A gas detector comprising the electrochemical cell of claim 10 and means for measuring the current flowing between the sensing electrode and the counter electrode, the measured current being indicative of the concentration of the gas detected.

17. The gas detector of claim 16, configured for detecting an oxidisable or reducible gas.

18. The gas detector of claim 16, operable for detecting one or more of ammonia, carbon monoxide, chlorine, diborane, fluorine, hydrazine, hydrogen, hydrogen cyanide, hydrogen fluoride, hydrogen selenide, hydrogen sulphide, hydrogen chloride, hydrogen bromide, arsine, mercaptan, nitric oxide, phosgene, phosphene, silane, and sulphur dioxide.

19. An electrochemical cell for detecting a gas from a surrounding environment, the cell comprising:
   an electrolyte;
   a sensing electrode in fluid communication with said electrolyte and a said gas to be detected, when present;
   a counter electrode in fluid communication with said electrolyte; and
   a source of reactant gas provided in a cavity adjacent to the counter electrode, wherein reaction of said gas to be detected at the sensing electrode results in reaction of the reactant gas at the counter electrode; and wherein the cavity is formed of or comprises a gas permeable or semi-permeable membrane configured for replenishment of the reactant gas with only gas from the electrolyte through the gas permeable or semi-permeable membrane.

* * * * *